United States Patent
Shiloach et al.

(10) Patent No.: US 7,202,199 B2
(45) Date of Patent: *Apr. 10, 2007

(54) ISOTROPIC CLEANSING COMPOSITION WITH PARTICULATE OPTICAL MODIFIERS

(75) Inventors: Anat Shiloach, Norwalk, CT (US); Rosa Paredes, Shelton, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 133 days.

This patent is subject to a terminal disclaimer.

(21) Appl. No.: 10/814,880

(22) Filed: Mar. 31, 2004

(65) Prior Publication Data

US 2005/0227880 A1    Oct. 13, 2005

(51) Int. Cl.
*C11D 9/20* (2006.01)
*C11D 1/02* (2006.01)
*C11D 1/88* (2006.01)
*C11D 3/37* (2006.01)
*C11D 3/14* (2006.01)

(52) U.S. Cl. ............ 510/159; 510/121; 510/123; 510/127; 510/151; 510/155; 510/426; 510/433; 510/475; 424/70.5; 424/70.11; 424/70.19

(58) Field of Classification Search .......... 510/121, 510/123, 127, 151, 155, 159, 426, 433, 475; 424/70.5, 70.11, 70.19
See application file for complete search history.

(56) References Cited

U.S. PATENT DOCUMENTS

| | | |
|---|---|---|
| 5,154,849 A | 10/1992 | Visscher et al. |
| 5,759,524 A | 6/1998 | Tanner et al. |
| 5,776,871 A | 7/1998 | Cothran et al. |
| 5,910,472 A | 6/1999 | Elliott et al. |
| 5,952,286 A | 9/1999 | Puvvada et al. |
| 6,083,491 A | 7/2000 | Mellul et al. |
| 6,172,019 B1 | 1/2001 | Dehan et al. |
| 6,277,360 B1 | 8/2001 | Carew et al. |
| 6,348,188 B1 | 2/2002 | Eccleson et al. |
| 6,395,691 B1 | 5/2002 | Tsaur |
| 6,451,300 B1 | 9/2002 | Dunlop et al. |
| 6,737,394 B2 * | 5/2004 | Shana'a et al. ............. 510/417 |
| 6,906,015 B1 * | 6/2005 | Shiloach et al. ............ 510/130 |
| 2003/0134759 A1 | 7/2003 | Geary et al. |
| 2003/0171231 A1 | 9/2003 | Shana'a et al. |

FOREIGN PATENT DOCUMENTS

| | | |
|---|---|---|
| EP | 0 463 780 | 1/1992 |
| EP | 463780 * | 1/1992 |
| EP | 1 384 470 | 1/2004 |
| GB | 1 228 060 | 4/1971 |
| GB | 2 283 755 | 5/1995 |
| WO | 97/29726 | 8/1997 |
| WO | 98/04237 | 2/1998 |
| WO | 03/039499 | 5/2003 |

OTHER PUBLICATIONS

J6773 (C) co-pending U.S. Appl. No. 10/241,401, Zhang et al. Oil-Containing Personal Wash Liquid Compositions or Emulsions Comprising Particles of High Refractive Index and Defined Thickness, Geometry and Size.
J6843 (C), U.S. Appl. No. 10/443,396, Zhang et al., Personal Product Compositions Comprising Structured Benefit Agent Premix or Delivery Vehicle and Providing Enhanced Effect of Optical Modifier Separate From the Structured Benefit Agent.
Shiloach, et al., J6894 (C), U.S. Appl. No. 10/814,064, Ordered Liquid Crystalline Cleansing Composition With Particulate Optical Modifiers.
International Search Report, PCT/EP2005/003243, mailed Jul. 5, 2005, 2 pp.

* cited by examiner

*Primary Examiner*—Brian Mruk
(74) *Attorney, Agent, or Firm*—Alan A. Bornstein

(57) ABSTRACT

An aqueous isotropic liquid cleansing and moisturizing composition is provided having a surfactant; a thickening agent, and a solid particulate optical modifier that modifies the appearance of the skin after wash off.

25 Claims, No Drawings

ISOTROPIC CLEANSING COMPOSITION WITH PARTICULATE OPTICAL MODIFIERS

BACKGROUND OF THE INVENTION

1. Field of the Invention

The present invention relates to detergent compositions suitable for topical application for cleansing the human body, such as the skin and hair. In particular, it relates to isotropic compositions containing particulate optical modifier(s) that changes the appearance of the skin after wash off.

2. Background of the Art

The visual appearance of skin is normally changed by using personal care compositions that are left on the skin. However, it would be useful if the visual appearance of skin could also be changed by using cleansing compositions that are washed off the skin. Such products would be beneficial to consumers who are looking for multiple functionalities in their cleansing products, such as cleansers that simultaneously cleanse and moisturize. In this case, products that cleanse the skin will also make it shine, sparkle, or glow by leaving behind solid particles that affect the interaction of light with the skin. These cleansers would save consumers the time required to apply a leave-on product that will change the visual appearance of the skin, and will also give them the benefit of appearing more attractive. Optionally, these cleansers could also contain moisturizers and emollients to condition the skin and one or more active agents which can be used to deliver a benefit to the skin and which generally are not used to confer a conditioning benefit.

Prior art skin cleansers modify the way the skin feels after the shower by depositing materials such as oils or polymers. Such materials deposit on the skin by various mechanisms, including attraction of cationic materials to the anionic surface of the skin. However, materials that change the feel of the skin do not generally change the look of the skin.

Surprisingly it has been discovered that by incorporating certain solid particles and a specific cationic polymer in a cleanser formulation, the visual appearance of the skin can be modified after wash off without the need for a complex delivery system employing specific oil droplets.

U.S. Pat. No. 6,395,691 issued to Tsaur on May 28, 2002 directed to a personal wash liquid formulation, discloses the use of a particle-in-oil dispersion to deliver solid particles to the skin that are effected by adjusting the size of the oil droplet and the size ratio between the oil droplet and the particles, and employs large droplets of petrolatum or thickened oil to deposit particles. The composition of Tsaur contains 2 to 20% by wt. of such a particle-in-oil dispersion.

In a co-pending U.S. patent application Ser. No. 10/443,396 filed on May 22, 2003 by Zhang et al. relating to the deposition of particles from a cleanser, the particles being deposited are small (under 20 microns) and the formulations disclosed rely on structured oil to deposit the particles. In another co-pending U.S. patent application Ser. No. 10/241,401 filed on Sep. 11, 2002 by Zhang et al. relating to the deposition of particles from a cleanser, the particles being deposited have a specified geometry and refractive index and the formulations disclosed rely on a particle-in-oil dispersion to deposit the particles. The present invention differs from Tsaur and Zhang et al. in that it does not employ either a particle-in-oil dispersion nor a structured oil to deposit particles as it's predominate deposition mechanism.

Cosmetic formulations that are left on the skin and contain solid particles to modify the skin appearance are well known. For example, many currently available lotions contain mica coated with titanium dioxide or iron oxide that make the skin sparkle. Wash-off cleanser formulations that contain solid particles to modify the appearance of the cleanser itself are also well known. For example, many currently available body wash products contain mica coated with titanium dioxide to give the product a shimmering appearance. In addition, cleanser formulations may contain solid particles to give the formulation abrasive characteristics and to exfoliate the skin. Many products that are marketed as exfoliating cleansers contain particles such as polyethylene or various fruit seeds to scrub the skin.

US Publication no. 2003/0134759 A1 published on Jul. 17, 2003 to Geary et al. describes a formulation that contains surfactant, water insoluble solid particles, a synthetic cationic polymer, and a phase separation initiator and which contains from about 0.025% to 5% by weight of an organic, non crosslinked, cationic homopolymer or copolymer having a cationic charge density of from about 2 meq/gm to about 10 meq/gm and an average molecular weight of from about 1,000 to about 5,000,000. The solid particles are deposited when the phase separation initiator causes the polymer to form a liquid crystal phase. Unlike Geary, the cleansing composition of the present invention does not contain a liquid crystal phase.

BRIEF DESCRIPTION OF THE INVENTION

In one aspect of the invention is an isotropic cleansing composition having:
  (a) about 1 to 35 wt. % of surfactant(s) selected from an anionic, nonionic, amphoteric or cationic surfactant or mixtures thereof;
  (b) a thickening agent;
  (c) about 0.1% to 10% of a cationic polymer;
  (d) an effective concentration of a solid particulate optical modifier for exhibiting a specific set of optical properties on skin characterized by a set of Tristimulus Color Values L, a*, and b*; a reflectivity change, and an opacity change, that provides at least a 5% change in at least one of the specific optical properties when said cleansing composition is applied to skin and then rinsed off using the In-vitro Visual Assessment Protocol; and
  (e) wherein the viscosity of the isotropic cleansing composition is in the range of about 1,000 to 300,000 cps @ 1/sec shear rate at 25 C.

In another aspect of the invention is a method of depositing a solid particulate optical modifier from an isotropic liquid cleansing composition onto the skin, including the steps of:
  (a) providing said solid particulate optical modifier in said cleansing composition including:
    1) a surfactant selected from anionic, nonionic, amphoteric and cationic surfactants, and mixtures thereof;
    2) a thickening agent,
    3) about 0.2% to about 1% by weight of said solid particulate optical modifier of from about 50 to about 150 microns in average diameter; and
    4) about 0.1% to 10% of a cationic polymer;
  (b) applying said cleansing composition to the skin or hair; and
  (c) rinsing off said cleansing composition.

DETAILED DESCRIPTION OF THE INVENTION

In one aspect of the invention is an isotropic cleansing composition having:

(a) about 1 to 35 wt. % of surfactant(s) selected from an anionic, nonionic, amphoteric or cationic surfactant or mixtures thereof;

(b) a thickening agent;

(c) about 0.1% to 10% of a cationic polymer;

(d) an effective concentration of a solid particulate optical modifier for exhibiting a specific set of optical properties on skin characterized by a set of Tristimulus Color Values L, a*, and b*; a reflectivity change, and an opacity change, that provides at least a 5% change in at least one of the specific optical properties when said cleansing composition is applied to skin and then rinsed off using the In-vitro Visual Assessment Protocol; and (e) wherein the viscosity of the isotropic cleansing composition is in the range of about 1,000 to 300,000 cps @ 1/sec shear rate at 25 C.

Advantageously, the visual attribute targeted by the optical modifier is selected from skin shine, skin color or skin optical uniformity, and combinations thereof.

Preferably in the case of conferring a skin shine benefit, the change in L value is in the range from about 0 to ±10, the reflectance change in the range from about 0 to ±300%, and the change in opacity in the range from about 0 to ±20% with the proviso that the change in L value, reflectance change and opacity change are not all zero so as to provide noticeable skin shine when said cleansing composition is applied to skin and then rinsed off using the In-vitro Visual Assessment Protocol. For skin shine preferably greater than about 10% (preferably greater than about 20, 30, 40, 50, 60, 70, 80, 90 or 95%) by wt. of the particulate optical modifier is further defined by an exterior surface refractive index, geometry, and specific dimensions wherein:

i) the exterior surface has a refractive index of about 1.8 to 4.0;

ii) the geometry is platy, cylindrical or a blend thereof; and iii) the specific dimensions are about 10 to 200 um average diameter in the case of a platy particle, or about 10 to 200 um in average length and about 0.5 to 5.0 um in average diameter in the case of a cylindrical particle.

Preferably in the case of conferring a noticeable skin lightening or color change to the skin the change in L value is in the range from about 0 to ±10, the change in the a* value is in the range from about 0 to ±10, a change in the b* value in the range from about 0 to ±10, the change in opacity in the range from about 0 to ±50%, and the reflectance change is within the normal skin reflectivity range of about ±10%, with the proviso that the change in L value, b* and opacity change are not all zero so as to provide noticeable skin lightening or color change when said cleansing composition is applied to skin and then rinsed off using the In-vitro Visual Assessment Protocol. For skin lightening or color change, preferably greater than about 10% (preferably greater than about 20, 30, 40, 50, 60, 70, 80, 90 or 95%) by wt. of the particulate optical modifier is further defined by an exterior surface refractive index, geometry, and specific dimensions wherein:

i) the exterior surface has a refractive index of about 1.3 to 4.0 ii) the geometry is spheroidal, platy or a blend thereof iii) the specific dimensions are about 1 to 30 um average diameter in the case of a platy particle, or about 0.1 to 1 um in average diameter in the case of a spheroidal particle; and iv) optionally having fluorescence color, absorption color, interference color or a combination thereof.

Preferably in the case of conferring a noticeable skin optical uniformity change the change in L value is in the range from about 0 to ±5, the reflectance change is in the range from about 0 to ±100%, the change in opacity is in the range from about 0 to ±50%, and the change in a* and b* are within normal skin color range of about ±10% for each of a* or b*, with the proviso that the change in L value, reflectance change and opacity change are not all zero so as to provide noticeable skin optical uniformity change when said cleansing composition is applied to skin and then rinsed off using the In-vitro Visual Assessment Protocol. For a noticeable skin optical uniformity change, preferably greater than about 10% (preferably greater than about 20, 30, 40, 50, 60, 70, 80, 90 or 95%) by wt. of the particulate optical modifier is further defined by an exterior surface refractive index, geometry, and specific dimensions wherein:

i) the exterior surface has a refractive index of about 1.3 to 2.0 ii) the geometry is spheroidal, platy, cylindrical or a blend thereof iii) the specific dimensions are, about 0.1 to 200 um in average diameter in the case of a spheroidal particle, about 1 to 10 um average diameter in the case of a platy particle, or about 1 to 10 um in average length and about 0.5 to 5.0 um in average diameter in the case of a cylindrical particle, and iv) optionally having fluorescence color, absorption color, interference color or a combination thereof.

Advantageously the cationic polymer has a charge density of at least about 0.7 Meq/g, preferably at least about 0.8, 0.9 or 1.0 Meq/g. Preferably the inventive composition contains an anionic surfactant and the ratio of anionic surfactant to a surfactant that has a positive charge at a pH of about 6.5 or below is in the range of about 15:1 to about 1:2 (preferably where the surfactant has a positive charge at a pH of about 5.5 or below). More preferably the surfactant with the positive charge is an amphoteric surfactant. Most preferably, the amphoteric surfactant is selected from betaine, alkylamidopropyl betaine, sulphobetaine, amphoacetate or blends thereof.

In a further embodiment, the inventive composition further includes an emollient having a weight average emollient particle size in the range of about 1 to about 500 microns. Preferably the water content of the inventive composition is greater than about 30% by weight. More preferably the viscosity of the inventive cleansing composition is in the range of about 5,000 to about 50,000 cps.

Advantageously the solid particulate optical modifier has an average diameter of at least about 30 microns. (preferably at least about 40, 50, 60, 70, 80, 90, 100, 120, 140, or 150 microns). In a preferred embodiment, the solid particulate optical modifier is present in a minimum concentration of at least about 0.2% by wt. (preferably at least about 0.25, 0.3, 0.4, 0.5, 0.7, 0.9, or 1% by wt.).

The thickening agent is preferably selected from polyacrylates; silica, natural and synthetic waxes; aluminum silicate; lanolin derivatives; C8 to C20 fatty alcohols polyethylene copolymers; polyammonium carboxylates; sucrose esters; hydrophobic clays; petrolatum; hydrotalcites; cellulose derivatives, polysaccharide derivatives, or derivatives and mixtures thereof. Advantageously the inventive composition is structured with a structurant selected from swelling clays; cross-linked polyacrylates; acrylate homopolymers and copolymers; polyvinylpyrrolidone homopolymers and copolymers; polyethylene imines; inorganic salts; sucrose esters, gellants or blends and derivatives thereof.

In a further preferred embodiment, the inventive composition contains less than about 50% by wt. (preferably less than about 40, 30, 20, 10, or 5% by wt.) of the solid particulate optical modifier is suspended in an oil. Preferably the composition contains less than about 10% by wt. (preferably less than 5, 2, 1, 0.5, 0.1 or 0.05% by wt.) of hydrophobic emollient(s) (as defined below).

Advantageously the anionic surfactant is selected from a C8–C16 alkyl sulfate and/or alkyl ether sulfates, fatty acid soaps, taurates, sulfosuccinates, glycinates, sarcosinates or derivatives or blends thereof. Preferably the composition has at least about 7 wt % of total surfactants.

Preferably the particulate optical modifier is selected from organic pigments, inorganic pigments, polymers, titanium oxide, zinc oxide, colored iron oxide, chromium oxide/hydroxide/hydrate, alumina, silica, zirconia, barium sulfate, silicates, polyethylene, polypropylene, nylon, ultramarine, alkaline earth carbonates, talc, sericite, mica, synthetic mica, polymers, platy substrate coated with organic and inorganic materials, bismuth oxychloride, barium sulfate, or blends and physical aggregates thereof. In a preferred embodiment the particulate optical modifier possesses color generated through fluorescence, adsorption, iridescence or a combination thereof.

In a further preferred embodiment, the particulate optical modifier is composed predominately of platy particles further defined by having an average plate diameter of about 10 um to 200 um and a refractive index of at least about 1.8 (preferably having an average plate diameter of about 10 um to 100 um and a refractive index of at least about 2).

Advantageously the cationic polymer is selected from Merquat® 100 or 2200, Jaguar® C17 or C13S, Salcare® Supre 7, SC10, or SC30; Gafquat® HS100 or 755, and Luviquat® FC370, FC550, HM552 or FC905, or blends thereof and the like. Preferably the particulate optical modifier contains a surface modification selected from amino acids, proteins, fatty acids, lipids, phospholipids (lecithin), anionic and/or cationic oligomers/polymers or blends or derivatives thereof and the like to enhance the deposition of the optical modifier on to the skin. Preferably less than about 50, 40, 30, 20, 10 or 5% by wt. of the particulate optical modifier has a hydrophobic coating.

In another aspect of the invention is a method of depositing a solid particulate optical modifier from an isotropic liquid cleansing composition onto the skin, including the steps of:

(a) providing said solid particulate optical modifier in said cleansing composition including:
  (1) a surfactant selected from anionic, nonionic, amphoteric and cationic surfactants, and mixtures thereof;
  (2) a thickening agent,
  (3) about 0.2% to about 1% by weight of said solid particulate optical modifier of from about 50 to about 150 microns in average diameter; and
  (4) about 0.1% to 10% of a cationic polymer;
(b) applying said cleansing composition to the skin or hair; and
(c) rinsing off said cleansing composition.

Surfactants:

Surfactants are an essential component of the inventive cleansing composition. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

The cleansing composition of the present invention may contain one or more anionic detergents. Anionic surfactants are preferably used at levels as low as about 5 or 7% by wt., and at levels as high as about 12 or 15% by wt.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

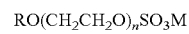

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

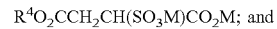

$$R^4O_2CCH_2CH(SO_3M)CO_2M; \text{ and}$$

amide-MEA sulfosuccinates of the formula;

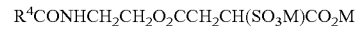

$$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula:

$$R^1CON(CH_3)CH_2CO_2M,$$

wherein $R^1$ ranges from $C_8$–$C_{20}$ alkyl and M is a solubilizing cation.

Taurates are generally identified by formula:

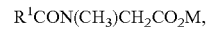

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

The inventive cleansing composition may contain $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

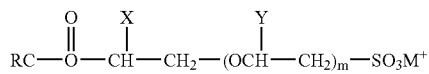

$$RC\overset{O}{\underset{\|}{-}}O-\overset{X}{\underset{|}{C}}H-CH_2-(OCH-CH_2)_m-SO_3M^+$$

wherein R is an alkyl group having 8 to 18 carbons, m is an integer from 1 to 4, X and Y are hydrogen or an alkyl group having 1 to 4 carbons and M⁺ is a monovalent cation such as, for example, sodium, potassium or ammonium.

Amphoteric Surfactants

One or more amphoteric surfactants may be used in this invention. Amphoteric surfactants are preferably used at levels as low as about 0.5 or 0.8, and at levels as high as about 4 or 5% by wt. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

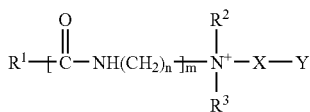

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric surfactants within the above general formula include simple betaines of formula:

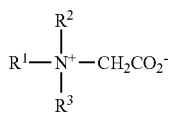

and amido betaines of formula:

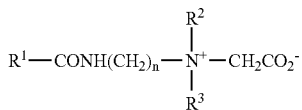

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

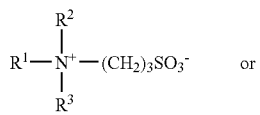

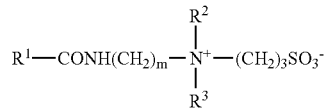

where m is 2 or 3, or variants of these in which —$(CH_2)_3$$SO_3^-$ is replaced by

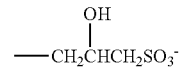

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Nonionic Surfactants

One or more nonionic surfactants may also be used in the cleansing composition of the present invention. Nonionic surfactants are preferably used at levels as low as about 0.5 or 0.8 and at levels as high as about 1.5 or 2% by wt.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Thickening Agents

Suitable thickening agents can be added as a structurant for the composition. Suitable thickening agents include polacrylates; fumed silica natural and synthetic waxes, alkyl silicone waxes such as behenyl silicone wax; aluminium silicate; lanolin derivatives such as lanesterol; C8 to C20 fatty alcohols; polyethylenecopolymers; polyammonium stearate; sucrose esters; hydrophobic clays; petrolatum; hydrotalcites; and mixtures thereof, and the like.

Hydrotalcites are materials of general formula:

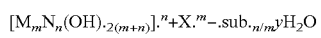

where

M is a divalent metal ion e.g. $Mg.^{2+}$;

N is a trivalent metal ion e.g. $Al.^{3+}$;

X is an exchangeable anion e.g. $CO_{\cdot3}.^-$, $NO_{\cdot3}.^-$, stearate;

m is the number of divalent metal ions; and n is the number of trivalent metal ions.

Particularly preferred thickening agents include silica, alkyl silicone waxes, paraffin wax, C8 to C20 fatty alcohols, petroleum jelly and polyethylene copolymers, blends thereof and the like.

While some materials can function as both an emollient and a thickener therefor it will be appreciated that the emollient and thickening function cannot be provided by the same component. However, it will be understood that where the composition comprises two or more emollients one of said emollients could also function as a thickening agent.

Preferably the amount of thickening agent may be as low as about 1% by wt. and up to about 5, 10, 15, 20 or 25% by weight.

Although the compositions of the invention may be self-structuring preferably they will also comprise a structurant, i.e. a material added to increase the viscosity at zero shear. Suitable materials include swelling clays, for example laponite; fatty acids and derivatives hereof and, in particular fatty acid monoglyceride polyglycol ethers; cross-linked polyacrylates such as Carbopol™ (polymers available from Goodrich); acrylates and copolymers thereof e.g. Aqua SF-1 available from Noveon (Cleveland, Ohio), polyvinylpyrrolidone and copolymers thereof; polyethylene imines; salts such as sodium chloride and ammonium sulphate; sucrose esters; gellants; natural gums including alginates, guar, xanthan and polysaccharide derivatives including carboxy methyl cellulose and hydroxypropyl guar; propylene glycols and propylene glycol oleates; glycerol tallowates; and mixtures thereof, mixtures thereof, and the like.

Of the clays particularly preferred are synthetic hectorite (laponite) clay used in conjunction with an electrolyte salt capable of causing the clay to thicken. Suitable electrolytes include alkali and alkaline earth salts such as halides, ammonium salts and sulphates, blends thereof and the like.

Further examples of structurants and thickeners are given in the International Cosmetic Ingredient Dictionary, Fifth Edition, 1993, published by CTFA (The Cosmetic, Toiletry & Fragrance Association), incorporated herein by reference.

Cationic Skin Conditioning Agents

A necessary component in compositions according to the invention is a cationic skin feel agent or polymer, such as for example cationic celluloses. Cationic polymers are preferably used at levels as low as about 0.2 or 0.3 and at levels as high as about 1 or 1.5% by wt.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation.

Cationic Surfactants

One or more cationic surfactants may also be used in the cleansing composition. Cationic surfactants may be used at levels as low as about 0.1, 0.3, 0.5 or 1 and at levels as high as 2, 3, 4 or 5% by wt.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

In addition, the inventive cleansing composition of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2', 4' trichlorodiphenylether (DP300); preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Moisturizers that also are humectants such as polyhydric alcohols, e.g. glycerine and propylene glycol, and the like; and polyols such as the polyethylene glycols listed below and the like may be used.

| Polyox WSR-205 | PEG 14M, |
| Polyox WSR-N-60K | PEG 45M, or |
| Polyox WSR-N-750 | PEG 7M. |

Hydrophobic and/or hydrophilic emollients (i.e. humectants) mentioned above may be used. Preferably, hydrophilic emollients are used in excess of hydrophobic emollients in the inventive cleansing composition. Most preferably one or more hydrophilic emollients are used alone. Hydrophilic emollients are preferably present in a concentration greater than about 0.01% by weight, more preferably greater than about 0.5% by weight. Preferably the inventive composition contains less than about 10, 5, 3, 2, 1, 0.7, 0.5, 0.3, 0.2, 0.1, 0.05 or 0.01% by wt. of a hydrophobic emollient.

The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful emollients (also considered conditioning compounds according to the invention) include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic and hydrophillic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as *mentha*, jasmine, camphor, white cedar, bitter orange peel, ryu, turpentine, cinnamon, bergamot, *citrus unshiu*, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, *calendula*, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) mixtures of any of the foregoing components, and the like.

Preferred conditioning agents are selected from glycerin, triglyceride oils, mineral oils, petrolatum, and mixtures thereof. Further preferred emollients are glycerin, triglycerides such as shea butter and sunflower seed oil.

Isotropic Micellar Phase Compositions:

The inventive cleansing composition possesses isotropic micellar phase microstructure. The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like or discoidal), spherocylindrical, or ellipsoidal micelles may form. As surfactant concentration increases, ordered liquid crystalline phases such as lamellar phase, hexagonal phase, cubic phase or L3 sponge phase may form. The non-isotropic hexagonal phase, consists of long cylindrical micelles arranged in a hexagonal lattice. In general, the microstructure of most personal care products consist of either an isotropic dispersion including spherical micelles; and rod micelles; or an ordered liquid crystalline phase such as a lamellar dispersion.

As noted above, micelles may be spherical or rod-like. Formulations having spherical micelles tend to have a low viscosity and exhibit Newtonian shear behavior (i.e., viscosity stays constant as a function of shear rate; thus, if easy pouring of product is desired, the solution is less viscous. In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means that the product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using isotropic micellar phases such as rod-micellar solutions; or lamellar dispersions. When rod-micellar solutions are used, they also often require the use of external structurants to enhance viscosity and to suspend particles. For this, carbomers and clays are often used. At higher shear rates (as in product dispensing, application of product to body, or rubbing with hands), since the rod-micellar solutions are less shear thinning, the viscosity of the solution stays high and the product can be stringy and thick.

One way of characterizing isotropic micellar dispersions (hereinafter "isotropic compositions") include cone and plate viscosity measurement as described below. The inventive isotropic composition has a viscosity in the range of about 1,000 to about 300,000 cps @ 1/sec shear rate at 25 C as measured by a cone and plate technique described below. Preferably the viscosity is in the range of about 5,000 to 50,000 cps.

Solid Particulate Optical Modifiers

An important component of compositions according to the present invention is that of solid particulate optical modifiers, preferably light reflecting platelet shaped or platy particles. These particles will preferably have an average particle size $D_{50}$ ranging from about 25,000 to about 150,000 nm. For plate-like materials the average particle size is a number average value. The platelets are assumed to have a circular shape with the diameter of the circular surface averaged over many particles. The thickness of the plate-like particles is considered to be a separate parameter. For instance, the platelets can have an average particle size of 35,000 nm and an average thickness of 400 nm. For purposes herein, thickness is considered to range from about 100 to about 600 nm. Laser light scattering can be utilized for measurement except that light scattered data has to be mathematically corrected from the spherical to the non-spherical shape. Optical and electron microscopy may be used to determine average particle size. Thickness is normally only determined via optical or electron microscopy.

The refractive index of these particles is preferred to be at least about 1.8, generally from about 1.9 to about 4, more preferably from about 2 to about 3, optimally between about 2.5 and 2.8.

Illustrative but not limiting examples of light reflecting particles are bismuth oxychloride (single crystal platelets) and titanium dioxide and/or iron oxide coated mica. Suitable bismuth oxychloride crystals are available from EM Industries, Inc. under the trademarks Biron® NLY-L-2×CO and Biron® Silver CO (wherein the platelets are dispersed in castor oil); Biron® Liquid Silver (wherein the particles are dispersed in a stearate ester); and Nailsyn® IGO, Nailsyn® II C2X and Nailsyn® II Platinum 25 (wherein the platelets are dispersed in nitrocellulose). Most preferred is a system where bismuth oxychloride is dispersed in a $C_2$–$C_{40}$ alkyl ester such as in Biron® Liquid Silver.

Among the suitable titanium dioxide coated mica platelets are materials available from EM Industries, Inc. These include Timiron® MP-45 (particle size range 49,000–57,000 nm), Timiron® MP-99 (particle size range 47,000–57,000 nm), Timiron® MP-47 (particle size range 28,000–38,000 nm), Timiron® MP-149 (particle size range 65,000–82,000 nm), and Timiron® MP-18 (particle size range 41,000–51,000 nm). Most preferred is Timiron® MP-149. The weight ratio of titanium dioxide coating to the mica platelet may range from about 1:10 to about 5:1, preferably from about 1:6 to about 1:7, by weight. Advantageously the preferred compositions will generally be substantially free of titanium dioxide outside of that required for coating mica.

Among the suitable iron oxide and titanium dioxide coated mica platelets are materials available from EM Industires, Inc. These include Timiron® MP-28 (particle size range 27,000–37,000 nm), Timiron® MP-29 (particle size range 47,000–55,000 nm), and Timiron® MP-24 (particle size range 56,000–70,000 nm). Most preferred is Timiron® MP-24.

Among the suitable iron oxide coated mica platelets are materials available from EM Industires, Inc. These include Colorona® Bronze Sparkle (particle size range 28,000–42,000 nm), Colorona® Glitter Bronze (particle size range 65,000–82,000 nm), Colorona® Copper Sparkle (particle size range 25,000–39,000 nm), and Colorona® Glitter Copper (particle size range 65,000–82,000 nm).

Suitable coatings for mica other than titanium dioxide and iron oxide may also achieve the appropriate optical properties required for the present invention. These types of coated micas must also meet the refractive index of at least about 1.8. Other coatings include silica on the mica platelets.

Optional Active Agents

Advantageously, active agents other than conditioning agents such as emollients or moisturizers defined above may be added to the cleansing composition in a safe and effective amount during formulation to treat the skin during the use of the product. These active ingredients may be advantageously selected from antimicrobial and antifungal actives, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; topical anesthetics, or mixtures thereof; and the like.

These active agents may be selected from water soluble active agents, oil soluble active agents, pharmaceutically-acceptable salts and mixtures thereof. Advantageously the agents will be soluble or dispersible in the cleansing composition. The term "active agent" as used herein, means personal care actives which can be used to deliver a benefit to the skin and/or hair and which generally are not used to confer a conditioning benefit, as is conferred by humectants and emollients previously described herein. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the composition of the present invention comprise from about 0.01% to about 50%, more preferably from about 0.05% to about 25%, even more preferably 0.1% to about 10%, and most preferably 0.1% % to about 5%, by weight of the active agent component.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4, 4'-trichloro-2'-hydroxy diphenyl ether, 3,4,4'-trichlorobanilide, phenoxyethanol, triclosan; triclocarban; and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters and pseudo-ceramides as described in European Patent Specification No. 556,957; ascorbic acid; biotin; biotin esters; phospholipids, mixtures thereof, and the like.

Non-steroidal cosmetic soothing actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyroxine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful as active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl(meth)acrylates, mixtures thereof, and the like.

Active ingredients in the present invention may also include anti-itch ingredients. Suitable examples of anti-itch ingredients which are useful in the compositions of the present invention include hydrocortisone, methdilizine and trimeprazineare, mixtures thereof, and the like.

Nonlimiting examples of hair growth inhibitors which are useful in the compositions of the present invention include 17 beta estradiol, anti angiogenic steroids, *curcuma* extract, cycloxygenase inhibitors, evening primrose oil, linoleic acid and the like. Suitable 5-alpha reductase inhibitors such as ethynylestradiol and, genistine mixtures thereof, and the like.

Nonlimiting examples of desquamating enzyme enhancers which are useful in the compositions of the present invention include alanine, aspartic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

The invention will now be described in greater detail by way of the following non-limiting examples. The examples are for illustrative purposes only and not intended to limit the invention in any way. Physical test methods are described below:

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

EXAMPLES

Examples of the inventive cleansing compositions (examples 1–7 below) were prepared and their stability and visual effect on skin and tile substrates after rinse off were compared to non-inventive compositions (examples 8–11 below). The inventive compositions were found to provide a significant change in skin and tile appearance compared to the comparative examples.

Examples 1–11

|  | Examples | | | | | | | | | | |
| --- | --- | --- | --- | --- | --- | --- | --- | --- | --- | --- | --- |
|  | 1 Inv. | 2 Inv. | 3 Inv. | 4 Inv. | 5 Inv. | 6 Inv. | 7 Inv. | 8 Com | 9 Com | 10 Com | 11 Com |
| Inventive/comparative Components (INCI name) (% Active by wt.) | | | | | | | | | | | |
| Ammonium Lauryl Sulfate (1) | 5.02 |  | 5.02 | 4.14 | 5.02 | 4.87 | 5.02 | 5.02 |  | 4.87 | 5.02 |
| Ammonium Laureth Sulfate (1) | 3.98 |  | 3.98 | 3.28 | 3.98 | 3.86 | 3.98 | 3.98 |  | 3.86 | 3.98 |
| Cocamide MEA (1) | 0.86 |  | 0.86 | 0.71 | 0.86 | 0.84 | 0.86 | 0.86 |  | 0.84 | 0.86 |
| PEG-5 Cocamide (1) | 0.43 |  | 0.43 | 0.36 | 0.43 | 0.42 | 0.43 | 0.43 |  | 0.42 | 0.43 |
| Sodium Laureth Sulfate (2) |  | 10 |  |  |  |  |  |  | 10.15 |  |  |
| Cocamidopropyl Betaine (3) | 1.8 | 2 |  | 1.5 | 1.8 | 1.5 | 1.8 | 0.8 | 2 | 1.5 | 0.8 |
| Acrylates Copolymer (4) | 1.2 | 1.2 | 1.2 | 1.4 | 1.2 | 1.2 | 1.2 | 1.5 | 1.2 | 1.2 | 1.5 |
| Guar Hydroxypropyltrimonium chloride (5) | 0.3 | 0.3 |  |  | 0.3 | 0.3 | 0.3 |  |  | 0.3 |  |
| Polyquaternium-6 (6) |  |  | 1.5 |  |  |  |  |  |  |  |  |
| Polyquaternium-10 (7) |  |  |  |  |  |  |  |  | 0.1 |  | 0.1 |
| Wheatgermamido propyl dimethylamine hydrolized wheat protein (8) |  |  |  | 0.2 |  |  |  |  |  |  |  |
| PEG-14M (9) |  |  |  | 0.15 |  |  |  |  |  |  |  |
| PEG-45M (10) |  |  |  |  |  | 0.05 |  |  |  |  |  |
| Mica and TiO2 (10–150 um) (11) | 0.5 | 0.5 | 0.45 | 0.45 | 0.9 | 0.45 |  |  |  |  |  |
| Mica and TiO2 and iron oxide (10–150 um) (12) |  |  | 0.05 | 0.05 | 0.1 | 0.05 | 0.5 |  |  |  |  |
| Mica and TiO2 (<50 um) (13) |  |  |  |  |  |  |  |  | 0.05 |  |  |
| Mica and TiO2 and iron oxide (10–150 um) (14) |  |  |  |  |  |  |  |  | 0.01 |  |  |
| Mica and TiO2 and iron oxide (5–100 um) (15) |  |  |  |  |  |  |  |  | 0.07 |  |  |
| Mica and TiO2 (5–25 um) (16) |  |  |  |  |  |  |  |  |  |  | 0.5 |
| Mica and TiO2 and triethoxy caprylylsilane (17) |  |  |  |  |  |  |  |  |  | 0.5 |  |
| Polyethylene (18) |  |  |  |  |  |  |  |  |  |  |  |
| Glycerin | 1 | 1 | 1 | 0.5 | 1 | 1.25 | 1 | 0.5 |  | 1.25 | 0.5 |
| Shea Butter | 0.01 |  |  |  |  |  |  | 0.01 |  |  |  |
| Divinyldimethicone/Dimethicone copolymer |  |  |  |  |  | 0.9 |  |  |  | 0.9 |  |
| Propylene glycol | 1.75 |  |  |  | 1.1 | 0.15 |  |  |  | 0.65 |  |
| Sodium chloride |  | 0.8 |  |  |  |  |  |  | 0.75 |  |  |
| Ammonium chloride |  |  | 1.1 | 0.2 |  |  |  | 0.2 |  |  | 0.5 |
| Methylchloroisothiazolinone and methylisothiazolinone ($\times 10^{-4}$) | 3 |  | 3 | 3 | 3 | 3 | 3 | 3 |  | 3 | 3 |
| DMDM Hydantoin |  | 0.1 |  |  |  |  |  |  |  |  |  |
| Sodium Benzoate |  |  |  |  |  |  |  |  | 0.5 |  |  |

-continued

| | | | | | | | | | | | |
|---|---|---|---|---|---|---|---|---|---|---|---|
| Tetrasodium EDTA ($\times 10^{-2}$) | 2 | 2 | 2 | 2 | 2 | 2 | 2 | 2 | | 2 | 2 |
| Citric acid | | | | | | | | | 0.4 | | |
| Sodium hydroxide ($\times 10^{-1}$) | 1 | | 0.4 | 0.2 | 0.2 | 1 | 1 | 2 | 0.75 | 1 | 1.5 |
| Benzophenone-4 | | | | | | | | 0.1 | | | |
| Fragrance | 1.3 | 0.9 | 0.6 | 0.8 | 0.6 | 0.6 | 0.6 | 1.3 | 0.9 | 0.6 | 0.6 |
| Water | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 |
| Properties | | | | | | | | | | | |
| Viscosity ($\times 10^4$), cps (21) | 2.3 | | 1.97 | 1.5 | 2.35 | 2.34 | | 1.9 | 0.94 | 2.45 | 1.45 |
| pH (25 C) | 5.5 | 5.5 | 5.5 | 6.6 | 5.5 | 6.5 | 5.4 | 6.3 | 4.6 | 6.7 | 6.6 |
| Stability (yes/no) (22) | yes | yes (22a) | yes | yes | yes (22a) | yes | yes (22a) | yes | yes | no | yes |
| Visual effect determination (yes/no, method used) (23) | Yes, con | Yes, con | Yes, lab | Yes, con | Yes, lab | Yes, tile/lab | No, lab | No, tile/lab | No, con | No, tile | No, tile/lab |
| Glitter count (24) | 5 | | | | | | | | | | 5 |

Notes:

(1) ALMEO blend — Stepan
(2) EMAL 270 — Huntsman
(3) Tegobetaine F — Goldschmidt
(4) Aqua SF-1 — Noveon
(5) Jaguar C13S — Rhodia
(6) Merquat 100 — Ondeo Nalco
(7) Polymer JR-400 — Amerchol
(8) Mackpro WWP — McIntyre
(9) Polyox WSR N-3000 — Amerchol
(10) Polyox WSR N-60K — Amerchol
(11) Timiron MP-149 — EMD Chemicals
(12) Colorona Glitter Copper — EMD Chemicals
(13) Flamenco Ultra Sparkle 4500 — Englehard
(14) Timiron MP-24 — EMD Chemicals
(15) Timiron MP-25 — EMD Chemicals
(16) Timiron MP-1001 — EMD Chemicals
(17) Timiron MP-1001AS — Cardre
(18) Microthene MN711/20 — Equistar
(19) Cetiol SB-45 — Cognis
(20) HMW 2220 Nonionic Emulsion — Dow Corning
(21) Brookfield RVDV-I+, CP 41, 0.5 rpm; 25° C.
Viscosity is adjusted by adding salt (s) such as ammonium chloride or sulfate or sodium chloride to increase viscosity and propylene glycol to decrease viscosity as the case may be.
(22) Stability test (see method below)
(22a) evaluated for stability only at room temperature, and only by visual inspection (not viscosity) and were stable.
(23) Yes/No: see criteria in method discussion below. Methods: con = consumer evaluation, lab = lab evaluation, tile = tile evaluation, tile/lab = tile and lab evaluation
(24) See glitter count method below.

Example preparation details:

Examples 1, 6, and 8:

Add water (49%) and start heating to 55° C.
Add Aqua SF1 polymer
At 55° C., add ALMEO blend; mix 10–20 min
Add shea butter
Add betaine
Add quench water (15% of batch)
Add NaOH soln
Add Jaguar submix (Jaguar, glycerin, propylene glycol)
Add Timiron submix (Timiron + 2% water)
Add Versene 100
Adjust pH to 5.5
At 45° C., add Kathon
At 40° C., add fragrance
Adjust viscosity to 18,000–25,000 cps Example 2:

Add water (37.6%) and start heating to 60° C.
Add Aqua SF1 polymer
Add EDTA
Add betaine
Add SLES at 60° C.
Mix until homogeneous
Add water (30%)

-continued

Add NaCl
Add glycerin/Jaguar submix
Add NaOH
Add Timiron/water premix (Timiron + 2% water)
Under 45° C. add Glydant
At 40° C., add fragrance
Adjust pH to 5.5
Adjust viscosity to 10,000 cps Example 3:

Add water (37.6%) and start heating to 60° C.
Add Aqua SF1 polymer
Add EDTA
Add betaine
Add SLES at 60° C.
Mix until homogeneous
Add water (30%)
Add NaCl
Add NaOH
Add Timiron/water premix (Timiron + 2% water)
Under 45° C. add Glydant
At 40° C., add fragrance
Adjust pH to 5.5
Adjust viscosity to 10,000 cps
Add polyethylene particles Example 4:

Add water (47%) and start heating to 55° C.
Add Aqua SF1 polymer
At 55° C., add ALMEO blend; mix 10–20 min
Add glycerin
Add Versene 100
Add water (15%)
Add betaine/Merquat 100 submix
Slowly add Timiron/water submix (Timiron + 2% water)
Adjust pH to 5.5
At 45° C., add Kathon
At 40° C., add fragrance
Adjust viscosity to 18,000–25,000 cps Example 5:

Add water (50%)
Add Aqua SF-1
Add Almeo
Begin to heat to 65° C.
Once at Temp and dissolved add all of NaOH
Add Glycerin/Polyox submix mix
Add Versene
Add Remaining water
Add Betaine
Add Mackpro
Add Timiron/water submix (Timiron + 2% water)
Let cool
At 45° C., add Kathon
At 40° C., add fragrance Example 7:

Add water (47%) and start heating to 60° C.
Add Aqua SF1 polymer
Add ALMEO blend; mix 10–20 min
Add glycerin/Polyox submix (0.5% glycerin)
At 60° C. and dissolved add NaOH
Add Versene
Add water (20%)
Add betaine
Add Jaguar/0.75% glycerin/propylene glycol premix
Let cool
At 45° C. add Kathon
Add Timiron premix
At 40° C. add fragrance
Add HMW 2220
Adjust pH to 6.5
Adjust viscosity to 18,000–24,000 cps Examples 9 and 12:

Add water (56%) and start heating to 55° C.
Add Aqua SF1 polymer
At 55° C., add ALMEO blend; mix 10–20 min
Add shea butter -continued Add Versene 100
Add quench water (14%)
Add betaine
Add glycerin
Add Uvinul
At 45° C., add Kathon
At 40° C., add fragrance/polymer JR400 submix
Add NaOH solution to pH 6.5
Add Flamenco/water submix (2% water)
Adjust viscosity to 14,000–19,000 cps
Example 10:

Add water (39%) and start heating to 60° C.
Add Aqua SF1 polymer
Add betaine
Add SLES
Mix until homogeneous
Add water (30%)
Add NaOH solution
Add NaCl solution
Add Timiron/water premix (2% water)
At 45° C., add sodium benzoate
Add citric acid
Add Euperlan
Add fragrance
Adjust pH to 4.7
Adjust viscosity to 10,000 cps
Example 11:

Add water (47%) and start heating to 60° C.
Add Aqua SF1 polymer
Add ALMEO blend; mix 10–20 min
Add glycerin (0.5%)
At 60° C. and dissolved add NaOH
Add Versene
Add water (20%)
Add betaine
Add Jaguar/0.75% glycerin/propylene glycol premix
At 45° C. add Kathon
At 40° C. add fragrance
Add HMW 2220/Timiron premix
Adjust pH to 6.5
Adjust viscosity to 18,000–24,000 cps Methods:

Stability Method:

Samples are stored at the following conditions and evaluated at the following time points.

| Condition | Time | Evaluations | Evaluation Points |
|---|---|---|---|
| Room Temperature | 12 weeks | Viscosity, Visual | Initial<br>1 day<br>1, 2, 4, 8, 12 weeks |
| 40° C. | 12 weeks | Visual only | 1, 2, 4, 8, 12 weeks |
| 50° C. | 1 week | Viscosity, Visual | 1 week |
| −9° C./25° C. cycle (24 hours at each temp.) | 3 cycles (6 days) | Viscosity, Visual | 1 week |

Viscosity: Measured by the method indicated for each example
Visual evaluation: color, odor, and appearance A sample is considered stable if its viscosity and visual evaluation do not change significantly (i.e. greater than 20% relative) from the initial measurements at all conditions.

Tile Method:

Prepare clay tiles with tan colored Sculpey II Polymer Clay (Polyform Products, Elk Grove, Ill.) by kneading clay, then rolling to a uniform thickness (2–3 mm) with a rolling pin. Cut 1" by 1" squares and press down 100 grain sandpaper on each square to make an even impression of the sandpaper on the clay. Bake for 15 minutes at 120 C and cool.

Wash tiles by placing 0.1 g product on a wet tile. Add 0.2 g water and rub for 15 seconds with a latex gloved finger. Rinse with tap water at about 35–45 C at a flow rate of 13–14 ml/sec, holding the tile 5 cm away at a 45-degree angle. Blot once with a paper towel and air dry for 15 minutes. Visually evaluate the quantity of optical particles left on the tiles.

Yes=At least 15 sparkles visible on a tile

No=less than this value

Hand Wash (Consumer Evaluation) Method

Give the product to naive consumers to use according to the following instructions: "Use similar to your regular body wash, applying to wet skin, sponge, washcloth, or pouf. Work into a lather and rinse." Ask consumers if they saw any change in the appearance of their skin, e.g. whether their skin looked radiant, shimmery, lustrous, glowing, etc. Naive consumers are defined as consumers that have not been trained in any way—in the use of the product or in what to look for on the skin.

Yes=at least 51% of consumers report seeing a visual change

No=less than this value

Hand Wash (Lab Evaluation) Method

Dispense approximately 1.5 g product on wet hands. Rub hands together to generate lather, adding water as needed. Rinse hands under running water at 35–45 C until hands feel clean. Pat dry with paper towel. Inspect hands visually for optical particles left behind.

Yes=At least 5 sparkles/cm2 visible on hands

No=less than this value

Tile/lab evaluation method is a combination of the Tile evaluation method and the lab evaluation method.

In-Vitro Visual Assessment Protocol (Porcine/Pig Skin Assay):

Take a piece of black porcine skin (L=40±3) with the dimensions of 5.0 cm×10 cm and mount it on a black background paper card. Initial measurements are made of the untreated skin. The mounted skin is then washed 1 to 2 minutes with "normal" rubbing with the composition to be tested and rinsed for about ½ minute with 45 C tap water. After 2 hours of drying at 25 C, the final measurements for color L, a*, b*; reflectivity and opacity are made.

Color Measurements:

The initial and final color measurements of porcine or in-vivo human skin are made with a Hunter Lab spectracolormeter using a 0° light source and 45° detector geometry. The spectracolormeter is calibrated with the appropriate black and white standards. Measurements are made before and after the wash treatment. Three measurements are made each time and averaged. The values obtained are L, a*, b*, which come from the La*b* color space representation.

Opacity Determination:

The opacity of the skin treated by the cleansing composition can be derived from the hunter Lab color measurements. The opacity contrast value is calculated from the delta L (which is the change in whiteness after deposition) divided by 60 (which is the difference in L value of the skin and a pure white color).

Reflectance or Radiance Determination:

The initial and final reflectance/radiance measurement of porcine or in-vivo human skin is made with a glossmeter before and after treatment with the cleansing composition. The glossmeter is first set with both the detector and light source at 85° from normal. Then the glossmeter is calibrated with an appropriate reflection standard. Measurements are made before and after application and rinsing off of the cleansing composition and the percent difference calculated.

Since a noticeable change in the skin when treated with the inventive composition may provide only scattered areas of skin appearance enhancement (such as point sparkle, glitter, etc.) instead of a continuous change over a wider expanse of the skin better suited to instrumental analysis using the glossmeter etc.; for the purposes of defining the level of skin appearance change required to be shown for the inventive composition, a "yes" result in either the Tile method, the Consumer method, the Hand wash (lab) method, or any combination thereof is to be considered equivalent to at least a 5% change in reflectivity when the inventive cleansing composition is applied to skin and then rinsed off using the In-vitro Visual Assessment Protocol.

In-Vivo Glitter Count:

Glitter count is a useful indicator regarding deposition but must be supplemented with other visual appearance methods to establish whether a sufficient change in visual appearance exists.

Method: Wash a 5 cm by 10 cm section of an inside forearm of a human panelist with the cleansing composition for 1 to 2 minutes with "normal" rubbing and rinse for about ½ minute with 45 C tap water. Let air dry for 20 min (no wiping) at 25 C. Then, under an intense light source or sunlight, count the number of sparkles seen in the washed area. The minimum number of sparkles counted considered for a "good" deposition is 2. The results are compared to a control consisting of the surfactant system and deionized water alone. The glitter count of the control is zero (i.e. no observable deposition).

Cone and Plate Viscosity Measurement

Scope:

This method covers the measurement of the viscosity of the isotropic phase cleansing composition.

Apparatus:

Brookfield Cone and Plate DV-II+ Viscometer;
Spindle S41;

Procedure:

1. Turn on Water Bath attached to the sample cup of the viscometer. Make sure that it is set for 25° C. Allow temperature readout to stabilize at 25° C. before proceeding.
2. With the power to the viscometer off, remove the spindle (S41) by turning counterclockwise.
3. Turn the power on and press any key as requested to autozero the viscometer.
4. When the autozero function is complete, replace the spindle (turning clockwise) and press any key.
5. Attach the sample cup. Using the up/down arrow keys, slowly change the speed to 10 rpm and press the SET SPEED key. Use the SELECT DISPLAY key so that the display is in % mode.
6. Turn the motor on. If the display jumps to 0.4% or higher or will not settle to 0±0.1%, turn the adjustment ring clockwise until it does.
7. Rotate the adjustment ring counterclockwise until the reading is fluctuating between 0.0 and 1.0%. The fluctuation must occur approximately every 6 seconds.
8. Turn the adjustment ring clockwise exactly the width of one division from the setting reached in step 7.
9. Turn the motor off. Using the up/down arrow keys, slowly change the speed to 0.5 rpm and press the SET SPEED key. Use the SELECT DISPLAY so that the display is in cP.
10. Place 2±0.1 g of product to be measured into the sample cup. Attach the cup to the viscometer.
11. Allow the product to remain in the cup with the motor OFF for 2 minutes.
12. Turn the motor ON and allow the spindle to turn for 2 minutes before noting the reading on the display.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:
1. An isotropic liquid cleansing composition comprising:
(a) about 1 to 35 wt. % of surfactant(s) selected from an anionic, nonionic, amphoteric or cationic surfactant or mixtures thereof;
(b) a thickening agent;
(c) about 0.1% to 10% of a cationic polymer;
(d) a solid particulate optical modifier in a concentration of at least about 0.2% by wt. for exhibiting a specific set of optical properties on skin characterized by one or more skin evaluation methods selected from Tile evaluation method, Hand wash (consumer evaluation) method, Hand wash (lab evaluation) method, or a set of Tristimulus Color Values L, a*, and b*; a reflectivity change, and an opacity change, that provides at least a 5% change in at least one of the specific optical properties when said cleansing composition is applied to skin and then rinsed off using the In-vitro Visual Assessment Protocol;
(e) wherein the viscosity of the isotropic cleansing composition is in the range of about 1,000 to 300,000 cps @ 1/sec shear rate at 25 C via the cone and plate method;
(f) less than 0.01% of a hydrophobic emollient; and
(g) wherein the solid particulate optical modifier is selected from organic pigments, inorganic pigments, platy substrate coated with organic and inorganic materials, or blends and physical aggregates thereof.

2. A composition according to claim 1 wherein the visual attribute targeted by the optical modifier is selected from skin shine, skin color or skin optical uniformity, and combinations thereof.

3. The composition according to claim 2 wherein the change in L value is in the range from about 0 to ±10, the reflectance change in the range from about 0 to ±300%, and the change in opacity in the range from about 0 to ±20% with the proviso that the change in L value, reflectance change and opacity change are not all zero so as to provide noticeable skin shine when said cleansing composition is applied to skin and then rinsed off using the In-vitro Visual Assessment Protocol.

4. The composition according to claim 2 wherein the change in L value is in the range from about 0 to ±10 the change in the a* value is in the range from about 0 to ±10, a change in the b* value in the range from about 0 to ±10 the change in opacity in the range from about 0 to ±50%, and the reflectance change is within the normal skin reflectivity range of about ±10% with the proviso that the change in L value, b* and opacity change are not all zero so as to provide noticeable skin lightening or color change when said cleansing composition is applied to skin and then rinsed off using the In-vitro Visual Assessment Protocol.

5. The composition according to claim 2 wherein the change in L value is in the range from about 0 to ±5, the reflectance change is in the range from about 0 to ±100%, the change in opacity is in the range from about 0 to ±50%, and the change in a* and b* are within normal skin color range of about ±10% for each of a* or b*, with the proviso that the change in L value, reflectance change and opacity change are not all zero so as to provide noticeable skin optical uniformity change when said cleansing composition is applied to skin and then rinsed off using the In-vitro Visual Assessment Protocol.

6. A composition according to claim 1 wherein the cationic polymer has a charge density of at least about 0.7 Meq/g.

7. A composition according to claim 1 wherein the composition contains an anionic surfactant and the ratio of anionic surfactant to a surfactant that has a positive charge at a pH of about 6.5 or below is in the range of about 15:1 to about 1:2.

8. A composition according to claim 7 wherein the surfactant with the positive charge is an amphoteric surfactant.

9. A composition according to claim 8 wherein the amphoteric surfactant is selected from betaine, alkylamidopropyl betaine, sulphobetaine, amphoacetate or blends thereof.

10. A composition according to claim 1 further comprising greater than about 30% by weight water.

11. A composition according to claim 1 wherein the viscosity of the cleansing composition is in the range of about 5,000 to about 50,000 cps.

12. A composition according to claim 1 wherein the solid particulate optical modifier has an average diameter of at least about 30 microns.

13. A composition according to claim 1 wherein the thickening agent is selected from polyacrylates; silica, natural and synthetic waxes; aluminum silicate; lanolin derivatives; C8 to C20 fatty alcohols polyethylene copolymers; polyammonium carboxylates; sucrose esters; hydrophobic clays; petrolatum; hydrotalcites; cellulose derivatives, polysaccharide derivatives, or derivatives and mixtures thereof.

14. A composition according to claim 1 wherein the composition is structured with a structurant selected from swelling clays; cross-linked polyacrylates; acrylate homopolymers and copolymers; polyvinylpyrrolidone homopolymers and copolymers; polyethylene imines; inorganic salts; sucrose esters, gellants or blends and derivatives thereof.

15. A composition according to claim 1 wherein less than about 50% by wt. of the solid particulate optical modifier is suspended in an oil.

16. A composition according to claim 7, wherein the anionic surfactant is selected from a C8–C16 alkyl sulfate and/or alkyl ether sulfates, fatty acid soaps, taurates, sulfosuccinates, glycinates, sarcosinates or derivatives or blends thereof.

17. A composition according to claim 1 having at least about 7 wt % of the surfactant.

18. The composition according to claim 1 wherein the particulate optical modifier possesses color generated through fluorescence, adsorption, iridescence or a combination thereof.

19. The composition according to claim 3 wherein greater than about 10% by wt. of the particulate optical modifier is further defined by an exterior surface refractive index, geometry, and specific dimensions wherein:
i) the exterior surface has a refractive index of about 1.8 to 4.0;
ii) the geometry is platy, cylindrical or a blend thereof; and
iii) the specific dimensions are about 10 to 200 um average diameter in the case of a platy particle, or about 10 to 200 um in average length and about 0.5 to 5.0 um in average diameter in the case of a cylindrical particle.

20. The composition according to claim 4 wherein greater than about 10% by wt. of the particulate optical modifier is further defined by an exterior surface refractive index, geometry, and specific dimensions wherein:
i) the exterior surface has a refractive index of about 1.3 to 4.0
ii) the geometry is spheroidal, platy or a blend thereof iii) the specific dimensions are about 1 to 30 um average diameter in the case of a platy particle, or about 0.1 to 1 um in average diameter in the case of a spheroidal particle; and iv) optionally having fluorescence color, absorption color, interference color or a combination thereof.

21. The composition according to claim 5 wherein greater than about 10% by wt. of the particulate optical modifier is further defined by an exterior surface refractive index, geometry, and specific dimensions wherein:

i) the exterior surface has a refractive index of about 1.3 to 2.0 ii) the geometry is spheroidal, platy, cylindrical or a blend thereof iii) the specific dimensions are about 0.1 to 200 um in average diameter in the case of a spheroidal particle, about 1 to 10 um average diameter in the case of a platy particle, or about 1 to 10 um in average length and about 0.5 to 5.0 um in average diameter in the case of a cylindrical particle, and iv) optionally having fluorescence color, absorption color, interference color or a combination thereof.

22. The composition according to claim 1 wherein the particulate optical modifier is composed predominately of platy particles further defined by having an average plate diameter of about 10 um to 200 um and a refractive index of at least about 1.8.

23. The composition according to claim 1 wherein the cationic polymer is selected from cationic cellulose polymer(s), salts of hydroxyethyl cellulose reacted with trimethyl ammonium substituted epoxide, polymeric quaternary ammonium salts of hydroxyethyl cellulose reacted with lauryl dimethyl ammonium-substituted epoxide, cationic polysaccharide polymer(s), guar hydroxypropyltrimonium chloride, hydroxypropylated cationic guar derivative(s) optionally containing a low level of substituent groups and/or cationic quaternary ammonium groups, or blends thereof.

24. The composition according to claim 1 wherein the particulate optical modifier contains a surface modification selected from amino acids, proteins, fatty acids, lipids, phospholipids (lecithin), anionic and/or cationic oligomers/polymers or blends or derivatives thereof to enhance the deposition of the optical modifier on to the skin.

25. A method of depositing a solid particulate optical modifier onto the skin from an isotropic liquid cleansing composition, comprising the steps of:

(a) providing said solid particulate optical modifier in said cleansing composition including:

(1) a surfactant selected from anionic, nonionic, amphoteric and cationic surfactants, and mixtures thereof;

(2) a thickening agent, (3) about 0.2% to about 1% by weight of said solid particulate optical modifier of from about 50 to about 150 microns in average diameter, wherein the solid particulate optical modifier is selected from organic pigments, inorganic pigments, platy substrate coated with organic and inorganic materials, or blends and physical aggregates thereof;

(4) about 0.1% to 10% of a cationic polymer; and (5) less than 0.01% of a hydrophobic emollient;

(b) applying said cleansing composition to the skin or hair; and (c) rinsing off said cleansing composition.

* * * * *